United States Patent [19]
Bellina

[11] 3,954,837
[45] May 4, 1976

[54] SUBSTITUTED ALLOPHANATES
[75] Inventor: Russell F. Bellina, Wilmington, Del.
[73] Assignee: E. I. Du Pont de Nemours and Company, Wilmington, Del.
[22] Filed: Oct. 12, 1973
[21] Appl. No.: 405,800

[52] U.S. Cl. .............................. 260/471 C; 71/98; 71/99; 71/100; 71/111; 260/453 R; 260/455 A; 260/470; 260/552 R; 260/553 A
[51] Int. Cl.² .............. C07C 127/19; C07C 155/02; C07C 157/09
[58] Field of Search ............. 260/455 A, 470, 471 C

[56] References Cited
UNITED STATES PATENTS
3,823,179  7/1974  Fuchs ............................ 260/471 C
3,879,190  4/1975  Fuchs ............................... 260/481

*Primary Examiner*—James A. Patten

[57] ABSTRACT

Allophanates of the formula:

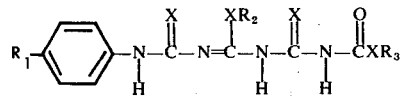

wherein:
 the X's are oxygen or sulfur;
 $R_1$ is hydrogen, certain organic radicals, or halogen; and
 $R_2$ and $R_3$ are certain organic radicals,
are useful for the control of flowering and plant sexual reproduction. A preferred use of the compounds of the present invention is to prevent corn inbreeding by applying the allophanate to the plant at or shortly before tassel emergence.

Exempliary of such compounds is: ethyl 4-[1-(4-chlorophenylcarbamoylimino)-1-(methoxymethyl)]allophanate.

5 Claims, No Drawings

SUBSTITUTED ALLOPHANATES

BACKGROUND OF THE INVENTION

Copending U.S. Pat. application Ser. No. 328,059, filed Jan. 30, 1973, by Kang Lin discloses the use of a class of allophanimidates of either of the following formulas:

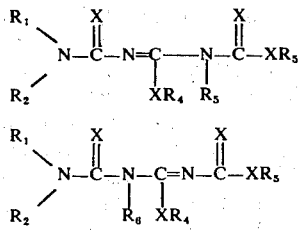

wherein:
the X's are oxygen or sulfur,
$R_1$ and $R_6$ are hydrogen or certain organic radicals, and
$R_2$, $R_4$, and $R_5$ are certain organic radicals, as plant regulants in that they alter plant flowering and/or plant sexual reproduction.

The present invention resulted from efforts to discover other novel, biologically active compounds.

SUMMARY OF THE INVENTION

This invention is a class of novel, biologically active compounds of the formula

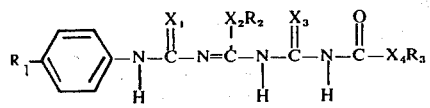

wherein:

$X_1$, $X_2$, $X_3$, and $X_4$ are each independently selected from oxygen or sulfur;
$R_1$ is hydrogen, halogen, alkyl of 1 through 4 carbon atoms, methoxy, or methylthio;
$R_2$ is alkyl of 1 through 3 carbon atoms; and
$R_3$ is alkyl of 1 through 3 carbon atoms.

The invention also includes compositions containing the above compounds as active ingredients, methods of controlling flowering and plant sexual reproduction by applying the compounds and/or compositions, and methods of preparing the compounds.

It should be understood that the following tautomeric form of the molecules represented by formula I is also possible:

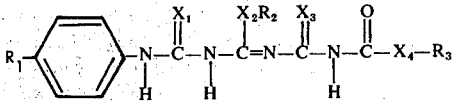

and that such form generally exists in equilibrium with the form represented by formula I. Accordingly, in the present invention, the schematic formula I is meant to include both tautomeric forms.

PREFERRED COMPOUNDS

Certain of the compounds of formula I above are preferred because of their ease of synthesis, higher activity, and lower phytotoxicity. These compounds include those where $X_1$ and $X_3$ are oxygen, $R_1$ is halogen, $R_2$ is methyl, and $R_3$ is methyl or ethyl.

Most preferred is ethyl 4-[1-(4-chlorophenylcarbamoylimino)-1-(methoxy)methyl]allophanate.

A preferred embodiment of this invention is a method of preventing inbreeding of corn, which comprises applying an allophanate of formula I to the corn before or at tassel emergence in an amount sufficient to prevent self-fertilization but insufficient to cause substantial foliar burn, chlorosis, or necrosis.

DETAILED DESCRIPTION OF THE INVENTION

Synthesis

The compounds of this invention can be prepared as illustrated by the following equations:

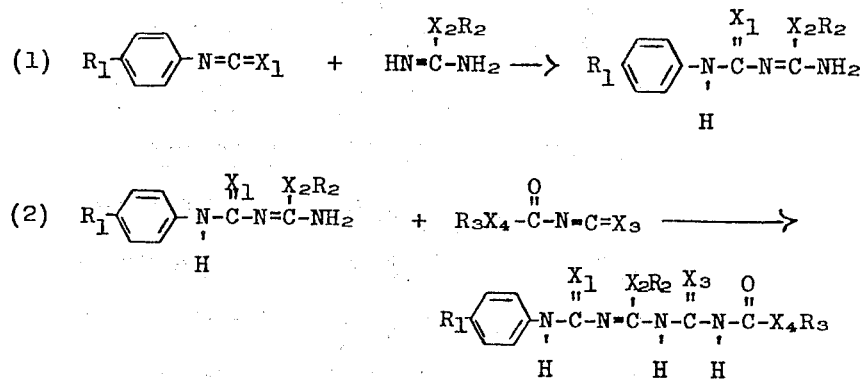

where $X_1$, $X_2$, $X_3$, $X_4$, $R_1$, $R_2$, and $R_3$ are as previously defined.

In equation (1) the pseudourea of 2-thiopseudourea is liberated from its corresponding chloride or sulfate salt with an equivalent amount of sodium hydroxide in a mixture of water and dichloromethane at 0° to 5°C. The isocyanate or isothiocyanate is then added and after stirring for 1 to 24 hours at room temperature the organic layer is separated, dried, and the solvent removed by evaporation to give the intermediate allophanimidate, thioallophanimidate, or dithioallophanimidate ester (This reaction is essentially the same as described in *Organic Synthesis*, 42, 87, for the preparation of methyl 4-phenyl-3-thioallophanimidate.

In equation (2) the intermediate allophanimidate is reacted with one equivalent of an alkoxycarbonyl isocyanate or isothiocyanate or an alkylthiolcarbonyl isocyanate or isothiocyanate in a dry inert solvent, for example, dichloromethane or tetrahydrofuran at room temperature for 1 to 24 hours. For those less reactive isothiocyanates (i.e., where $X_3$ is sulfur) longer reaction times, higher reaction temperatures, and/or the addition of a catalytic amount of a tertiary base, such as triethylamine, may be desirable. The solvent is removed by evaporation and the residue is recrystallized from a suitable solvent to afford the substantially pure alkyl 4-[1(arylcarbamoylimino)-1-(alkoxy)methyl]allophanates and their thio analogs of this invention. The alkoxycarbonyl and alkylthiolcarbonyl isocyanates can be prepared essentially as described in *Archi der Pharmazie*, 302, 691 (1969) for ethoxycarbonyl isocyanate; and the alkoxycarbonyl and alkylthiolcarbonyl isothiocyanates can be prepared essentially as described in *Journal of Organic Chemistry*, 29, 2264 (1964) for acyl isothiocyanates.

The following example is offered to illustrate the process described above. All parts are by weight.

EXAMPLE

Ethyl 4-[1-(4-chlorophenylcarbamoylimino)-1-(methoxy)-methyl]allophanate

320 Parts of a 50% sodium hydroxide solution was added dropwise to 345 parts of 2-methylpseudourea hydrogen sulfate in a mixture of 3500 parts of water and 4000 parts of dichloromethane which mixture was maintained at approximately 5°C. by a cooling bath. 307 Parts of p-chlorophenyl isocyanate was added to the resulting mixture and the cooling bath was removed. The reaction mas was stirred vigorously for 6 hours at room temperature. The dichloromethane layer was separated, dried over anhydrous sodium sulfate, and evaporated under reduced pressure. The residue was triturated in hexane and the solid was collected by filtration affording 400 parts of methyl 4-(4-chlorophenyl)allophanimidate, m.p. 115°–117°C.

12 Parts ethoxycarbonyl isocyanate was added dropwise to 23 parts of methyl 4-(4-chlorophenyl)allophanimidate (prepared as above) in 230 parts of tetrahydrofuran at 20°C. The mixture was stirred for six hours at room temperature and then evaporated under reduced pressure. The residue was triturated with boiling 1-chlorobutane, cooled, and the solid collected by filtration affording 16 parts of ethyl 4-[1-(4-chlorophenylcarbamoylimino)-1-(methoxy)methyl]allophanate, m.p. 140.5–142°C.

The following allophanates can be prepared by the above procedure by substituting the listed 2-substituted pseudoureas and thiopseudoureas for 2-methylpseudourea, by replacing p-chlorophenyl isocyanate with the listed isocyanates and isothiocyanates, and by replacing ethoxycarbonyl isocyanate with the listed alkoxycarbonyl and alkylthiolcarbonyl isocyanates and isothiocyanates.

| Pseudourea or Thiopseudourea | Isocyanate or Isothiocyanate | Alkoxycarbonyl or Alkylthiolcarbonyl Isocyanate or Isothiocyanate | Allophanate |
| --- | --- | --- | --- |
| 2-methylpseudourea | p-chlorophenyl isothiocyanate | methoxycarbonyl isocyanate | methyl 4-[1-(p-chlorophenyl-thiocarbamoylimino-1-(methoxy)methyl]allophanate |
| 2-methyl-2-thio-pseudourea | p-chlorophenyl isocyanate | methoxycarbonyl isocyanate | methyl 4-[1-(4-chlorophenyl-carbamoylimino)-1-(methylthio)-methyl]allophanate |
| 2-methylpseudourea | p-chlorophenyl isocyanate | ethoxycarbonyl isothiocyanate | ethyl 3-thio-4-[1-(4-chlorophenylcarbamoylimino)-1-(methoxy)methyl]allophanate |
| 2-methylpseudourea | p-chlorophenyl isocyanate | methylthiolcarbonyl isocyanate | methyl 1-thiol-4-[1-(4-chloro phenylcarbamoylimino)-1-(methoxy)methyl]allophanate |
| 2-methylpseudourea | p-chlorophenyl isocyanate | methylthiolcarbonyl isothiocyanate | methyl 1-thiol-3-thio-4-[1-(4-chlorophenylcarbamoylimino)-1-(methoxy)methyl]allophanate |
| 2-methylpseudourea | p-bromophenyl isocyanate | ethoxycarbonyl isocyanate | ethyl 4-[1-(4-bromophenyl-carbamoylimino)-1-(methoxy)methyl]allophanate |
| 2-methylpseudourea | p-fluorophenyl isocyanate | ethoxycarbonyl isocyanate | ethyl 4-[1-(4-fluorophenyl-carbamoylimino)-1-(methoxy)methyl]allophanate |
| 2-methylpseudourea | p-iodophenyl isocyanate | ethoxycarbonyl isocyanate | ethyl 4-[1-(4-iodophenyl-carbamoylimino)-1-(methoxy)methyl]allophanate |
| 2-methylpseudourea | p-methoxyphenyl isocyanate | ethoxycarbonyl isocyanate | ethyl 4-[1-(4-methoxyphenyl-carbamoylimino)-1-(methoxy)methyl]allophanate |
| 2-methylpseudourea | p-methylthiophenyl isocyanate | ethoxycarbonyl isocyanate | ethyl 4-[1-(4-methylthio-phenylcarbamoylimino)-1-(methoxy)methyl]allophanate |
| 2-methylpseudourea | 4-n-butylphenyl isocyanate | ethoxycarbonyl isocyanate | ethyl 4-[1-(4-n-butylphenyl-carbamoylimino)-1-(methoxy)methyl]allophanate |
| 2-methylpseudourea | p-tolyl isocyanate | ethoxycarbonyl isocyanate | ethyl 4-[1-(4-methylphenyl-carbamoylimino)-1-(methoxy)methyl]allophanate |
| 2-methylpseudourea | p-isopropylphenyl isocyanate | ethoxycarbonyl isocyanate | ethyl 4-[1-(4-isopropylphenyl-carbamoylimino)-1-(methoxy)methyl]allophanate |
| 2-methylpseudourea | p-ethylphenyl isocyanate | ethoxycarbonyl isocyanate | ethyl 4-[1-(4-ethylphenyl-carbamoylimino)-1-(methoxy)methyl]allophanate |
| 2-methylpseudourea | phenyl isocyanate | methoxycarbonyl isocyanate | methyl 4-[1-(phenylcarbamoyl-imino)-1-(methoxy)methyl]allophanate |
| 2-methylpseudourea | p-chlorophenyl isocyanate | methoxycarbonyl isocyanate | methyl 4-[1-(4-chlorophenyl-carbamoylimino)-1-(methoxy) |

-continued

| Pseudourea or Thiopseudourea | Isocyanate or Isothiocyanate | Alkoxycarbonyl or Alkylthiolcarbonyl Isocyanate or Isothiocyanate | Allophanate |
|---|---|---|---|
| 2-methyl-2-thio-pseudourea | p-chlorophenyl isocyanate | ethoxycarbonyl isocyanate | methyl]allophanate ethyl 4-[1-(4-chlorophenyl-carbamoylimino)-1-(methylthio) methyl]allophanate |
| 2-methylpseudourea | p-chlorophenyl isothiocyanate | ethoxycarbonyl isocyanate | ethyl 4-[1-(4-chlorophenyl-thiocarbamoylimino)-1-(methoxy) methyl]allophanate |
| 2-methylpseudourea | p-chlorophenyl isocyanate | ethoxycarbonyl isothiocyanate | ethyl 3-thio-4-[1-(4-chloro-phenylcarbamoylimino)-1-(methoxy)methyl]allophanate |
| 2-propylpseudourea | p-chlorophenyl isocyanate | ethoxycarbonyl isocyanate | ethyl 4-[1-(4-chlorophenyl-carbamoylimino)-1-(propoxy) methyl]allophanate |
| 2-isopropyl-2-thio-pseudourea | p-chlorophenyl isocyanate | ethoxycarbonyl isocyanate | ethyl 4-[1-(4-chlorophenyl-carbamoylimino)-1-(isopropylthio)methyl]allophanate |
| 2-methylpseudourea | p-chlorophenyl isocyanate | isopropoxycarbonyl isocyanate | isopropyl 4-[1-(4-chloro-phenylcarbamoylimino)-1-(methoxy)methyl]allophanate |
| 2-methyl-2-thio-pseudourea | p-chlorophenyl isothiocyanate | ethoxycarbonyl isocyanate | ethyl 4-[1-(4-chlorophenyl-thiocarbamoylimino)-1-methylthio)methyl]allophante |
| 2-methyl-2-thio pseudourea | p-chlorophenyl isothiocyanate | methoxycarbonyl isothiocyanate | methyl 3-thio-4-[1-(4-chlorophenylthiocarbamoyl-imino)-1-(methylthio)methyl] allophanate |
| 2-methyl-2-thio-pseudourea | p-chlorophenyl isothiocyanate | methylthiolcarbonyl isothiocyanate | methyl 1-thiol-3-thio-4-[1-(4-chlorophenylthio-carbamoylimino)-1-methyl-thio)methyl]allophanate |

Formulations of the Compounds

The formulations of the compounds of formula I for use in this invention can be prepared in conventional ways. They include dusts, granules, pellets, solutions, suspensions, emulsions, wettable powders, emulsifiable concentrates, and the like. Many of these may be applied directly. Sprayable formulations can be extended in suitable media and used as spray volumes of from a few pints to several hundred gallons per acre. High strength compositions are primarily used as intermediates for further formulations. The formulations, broadly, contain about 1 to 99% by weight of active ingredient(s) and at least one of (a) about 0.1 to 20% surfactant(s) and (b) about 1 to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower of high levels of active ingredients can, of course, be present, depending on the intended use and the physical properties of the compound. Higher ratios of surfactant to active ingredient are sometimes desirable and they are achieved by incorporation into the formulation or by tank mixing. Lower concentrations of active ingredient can aid in accurate application at the very low rates reached for this invention. Sprayable and dust formulations are preferred. Typical solid diluents are described in Watkins et al. "Handbook of Insecticde Dust Diluents and Carriers" Second Edition, Dorland Books, Caldwell, N.J. The more adsorptive diluents are preferred for wettable powders and the denser ones for dusts. Typical liquid diluents and solvents are described in Marsden "Solvents Dyed" Second Edition, Interscience, N.Y. (1950). Solubility under 0.1% is preferred for suspension concentrates; solutions concentrates are preferably stable against phase separation at 0°C. "McCutcheon's Detergents and Emulsifiers Annual" Allured Publishing Corporation, Ridgewood, N.J., as well as Sisely and Wood, "Encyclopedia of Surface Active Agents", Chemical Publishing Company, Inc., N.Y. (1964) list surfactants and recommended uses. All formulations can contain minor amounts of additives to reduce foam, caking, corrosion, microbiological growth, etc. Preferably, ingredients should be approved by the U.S. Environmental Protection Agency when food crop use is intended.

The methods of making such compositions are well known. Solutions are prepared by simply mixing the ingredients. Fine solid compositions are made by blending and usually grinding as in a hammer or fluid energy mill. Suspensions are prepared by wet milling (see, for example, Littler U.S. Pat. No. 3,060,084). Granules and pellets may be made by spraying the active material upon pre-formed granular carriers or by agglomeration techniques (see J. E. Browning, "Agglomeration," *Chemical Engineering*, Dec. 4, 1967, pp. 147 ff and "Perry's Chemical Engineers Handbook" 4th Edition, McGraw-Hill, New York, 1963, pp. 8–59 ff.).

For further information regarding the art of formulation see, for example,

H. M. Loux, U.S. Patent 3,235,361, Feb. 15, 1966, Col. 6, Line 16 through Col. 7, Line 19 and Examples 10 through 41.

R. W. Luckenbaugh, U.S. Patent 3,309,192, March 14, 1967, Col. 5, Line 43 through Col. 7, Line 62 and Examples 8, 12, 15, 39, 41, 52, 53, 58, 132, 138–140, 162–164, 166, 167, 169–182.

H. Gysin and E. Knusli, U.S. Patent 2,891,855, June 23, 1959, Col. 3, Line 66 through Col. 5, Line 17, and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

Typical formulations are shown in the following examples. All percentages are by weight.

EXAMPLE (A)

| Wettable Powder | Percent |
| --- | --- |
| ethyl 4-[1-(4-chlorophenylcarbamoylimino)-1-(methoxy)methyl]allophanate | 40 |
| dioctyl sodium sulfosuccinate | 1.5 |
| sodium ligninsulfonate | 3 |
| low viscosity methyl cellulose | 1.5 |
| attapulgite | 54 |

Thoroughly blend the ingredients then pass through an air mill to produce an average particle size under 15 microns. Reblend and sift through a U.S.S. No. 50 sieve (0.3 mm opening) before packaging.

All compounds of the invention may be formulated in the same manner.

EXAMPLE (B)

| High Strength Concentrate | Percent |
| --- | --- |
| methyl 4-[1-(phenylthiocarbamoylimino)-1-(methoxy)methyl]allophanate | 98.5 |
| silica aerogel | 0.5 |
| synthetic amorphous fine silica | 1.0 |

Blend and grind the ingredients in a hammer mill to produce a high strength concentrate essentially all passing a U.S.S. No. 50 sieve (0.3 mm openings). This material may then be formulated in a variety of ways.

EXAMPLE (C)

| Dust | Percent |
| --- | --- |
| high strength concentrate, Example (b) | 25.4 |
| pyrophyllite, powdered | 74.6 |

Thoroughly blend the ingredients and package for use.

EXAMPLE (D)

| Dust | Percent |
| --- | --- |
| Methyl 4-[1-(4-chlorophenylcarbamoylimino)-1-(methylthio)methyl]allophanate | 10 |
| attapulgite | 10 |
| talc | 80 |

The active ingredient is blended with attapulgite, passed through a hammer mill and the resulting product blended with powdered talc until homogeneous. All compounds of the invention may be formulated similarly.

EXAMPLE (E)

| Aqueous Suspension | Percent |
| --- | --- |
| ethyl 4-[1-(4-bromophenylcarbamoylimino)-1-(methoxy)methyl]allophanate | 25 |
| hydrated attapulgite | 3 |
| crude calcium ligninsulfonate | 10 |
| sodium dihydrogen phosphate | 0.5 |
| water | 61.5 |

Grind the ingredients together in a sand mill until the solid particles have been reduced to diameters under 10 microns

EXAMPLE (F)

| Oil Suspension | Percent |
| --- | --- |
| ethyl 4-[1-(4-chlorophenylcarbamoyl)-imino)-1-(methoxy)methyl]allophanate | 25 |
| polyoxyethylene sorbitol hexaoleate | 5 |
| highly aliphatic hydrocarbon oil | 70 |

Grind the ingredients together in a sand mill until the solid particles have been reduced to under about 5 microns. The resulting thick suspension may be applied directly, but preferably after being extended with oils or emulsified in water.

Use of the Invention

This invention can be used to facilitate the production of many hybrid seed crops. For example, in the production of hybrid corn seed, it can be used to prevent inbreeding. An allophanate of formula I is applied to the corn plant to be used as the female parent, preferably in a spray or dust formulation shortly before or at tassel emergence. This treatment substantially prevents pollen shed and may also destroy pollen viability, thus making it unnecessary to detassel. The invention can be used in a similar manner to prevent inbreeding of other crops plants, for example, rice and soybeans, by treating the plants at or near flowering with an allophanate of formula I.

The invention can also be used to alter fruit set pattern of various crops such as cotton, tomatos, citrus fruit, peaches, and apples. In these crops it is often desirable to prevent late fruit set for development in order to facilitate mechanical harvesting and/or eliminate the necessity of thinning. This can be accomplished by applying an allophanate of formula I to the plant after the desired amount of fruit set has taken place.

Similarly, the invention can be used to eliminate fruit set all together on certain types of ornamentals, for example, locusts and mimosa trees, where the fruit may be considered undesirable.

The invention can be used to prevent seed development in hay crops, such as alfalfa. This is considered desirable because the energy the plant would otherwise use to develop seeds can be used to increase forage development. Here again, the time to treat the plant is at or near flowering.

Another use for the invention is to prevent asparagus seed development. Asparagus plants are male or female. Female plants are about 20% less productive than male plants because of the energy utilized in seed development. By spraying plants at or just before flowering with a formulation of an allophanate of formula I fertilization and seed development can be substantially reduced or prevented, thus increasing yield of the female plants. Prevention of asparagus seed development is also desirable because otherwise the seeds are dropped, germinate, and the seedlings become a weed problem for the mature plants.

Presently, in new strawberry plantings the flowers are pinched off during the first year in order to prevent fruit set. Fruit hinders development of the strawberry plant bed. By use of this invention, that is, by applying an allophanate of formula I to the plants at or near flowering, the need for hand pinching the flower buds can be eliminated.

Another use of the invention is to prevent fruit set or seed development in certain crops which are not harvested for fruit or seed. For example, by applying one of the allophanates to potatos plants at or near flowering, fruit and seed development which interfere with tuber development can be prevented.

Still another use for the invention is to control pollen development and/or release in certain noxious leaves, for example, ragweed.

In this invention the allophanates of formula I are applied to the plant in an amount sufficient to produce the desired change in flowering and/or sexual reproduction but insufficient to cause substantial foliar burn, chlorosis, or necrosis. The allophanates vary in degree of phytotoxicity and the phytotoxicity of a given allophanate varies with the plant species. Thus, it is not possible to state a range of application rates which will be applicable for all allophanates and plant species. In general, rates in the range of about 0.1 to 10 kilograms per hectare will be used. The permissible rates for any combination of allophanates and plant species can be readily established empirically. The capability of an allophanate of formula I to affect flowering and sexual reproduction of plants is shown in the following greenhouse tests.

A foliar spray of ethyl 4-[1-(4-chlorophenylcarbamoylimino)-1-(methoxy)methyl]allophanate on Tenderette bush snap beans in the bud stage prevented fruit set four weeks with little effect on vegetative growth. Plants were about 24 days old and 25–30 centimeters tall when sprayed. Plants were passed under a fixed flat spray calibrated to deliver 230 liters per hectare. Plant response observations were recorded at three weeks and yields were recorded at four weeks.

| Compound | Rate kg/ha | 3-Week Response Rating[1] | Average Number of Fruit[2] |
|---|---|---|---|
| ethyl 4-[1-(4-chloro- | 2.24 | 2C,3G,RF | 0 |
| phenylcarbamoylimino)- 1-(methoxy)-methyl] allophanate | 0.56 0.14 0.04 | 1G,RF RF RF | 0 4 11.5 |
| Solvent control | — | 0 | 13 |

[1]G = growth retarded, C = chlorosis, RF = reduced fruiting, 0 = no effect, 10 = maximum response
[2]average of 4 replications (1 plant per replicate)

I claim:
1. Compounds of the formula:

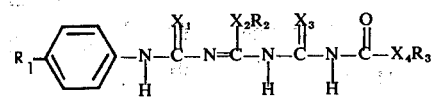

wherein
$X_1$, $X_2$, $X_3$, and $X_4$ and each independently selected from oxygen or sulfur;
$R_1$ is hydrogen, halogen, alkyl of 1 through 4 carbon atoms, methoxy or methylthio;
$R_2$ is alkyl of 1 through 3 carbon atoms; and
$R_3$ is alkyl of 1 through 3 carbon atoms.
2. The compounds of claim 1 wherein
$X_1$ and $X_3$ are oxygen;
$R_1$ is halogen,
$R_2$ is methyl; and
$R_3$ is methyl or ethyl.
3. Compounds of the formula:

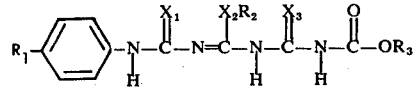

wherein
$X_1$, $X_2$, and $X_3$ are each independently selected from oxygen and sulfur;
$R_1$ is hydrogen, halogen, alkyl of 1 through 4 carbon atoms, methoxy, or methylthio;
$R_2$ is alkyl of 1 through 3 carbon atoms; and
$R_3$ is alkyl of 1 through 3 carbon atoms.
4. The compounds of claim 3 which is ethyl 4-[1-(4-chlorophenylcarbamoylimino)-1-(methoxy)methyl]allophanate.
5. The compounds of claim 3 wherein
$X_1$ and $X_3$ are oxygen;
$R_1$ is halogen;
$R_2$ is methyl; and
$R_3$ is methyl or ethyl.

* * * * *